United States Patent [19]

Huber

[11] Patent Number: 4,952,372

[45] Date of Patent: Aug. 28, 1990

[54] FLOW INJECTION APPARATUS FOR CARRYING OUT CHEMICAL ANALYSES

[75] Inventor: Bernhard Huber, Hildegardring, Fed. Rep. of Germany

[73] Assignee: The Perkin Elmer Corporation, Norwalk, Conn.

[21] Appl. No.: 219,429

[22] Filed: Jul. 14, 1988

[30] Foreign Application Priority Data

Jul. 14, 1988 [DE] Fed. Rep. of Germany ....... 3723178

[51] Int. Cl.⁵ .......................................... G01N 35/08
[52] U.S. Cl. ..................................... 422/81; 422/110; 422/82.09; 436/52
[58] Field of Search .......................... 422/68, 81, 110; 436/52; 73/863.01, 863.02, 863.03, 864.83, 864.84

[56] References Cited

U.S. PATENT DOCUMENTS

| | | | |
|---|---|---|---|
| 2,607,718 | 8/1952 | Suthard | 260/426 |
| 3,964,513 | 6/1976 | Molner | 73/864.83 |
| 4,346,705 | 8/1982 | Pekkarinen | 73/4 R |
| 4,424,276 | 1/1984 | Clark et al. | 436/50 |
| 4,486,097 | 12/1984 | Riley | 356/410 |
| 4,645,647 | 2/1987 | Yoshida et al. | 422/81 |
| 4,713,974 | 12/1987 | Stone | 422/81 |
| 4,830,218 | 5/1989 | Shirkhan | 222/52 |

Primary Examiner—Robert J. Warden
Assistant Examiner—D. John Griffith, Jr.
Attorney, Agent, or Firm—Thomas P. Murphy; Edwin T. Grimes

[57] ABSTRACT

In a flow injection analysis apparatus, the flow of reagent to a measuring apparatus is generated by means of a peristaltic pump. A sample liquid which is contained in a loop of tubing is introduced into the flow of reagent by a change-over valve with the loop being connected in a conduit of a carrier liquid. The measuring apparatus measures the reaction between sample liquid and reagent. The peristaltic pumps are driven by stepper motors. The stepper motors are controlled by control electronics such that nonuniformities of the delivery of the peristaltic pumps caused by geometry are compensated by inverse nonuniformities of the angular rates. For that purpose the frequencies of the switching pulses are varied depending on position sensors.

13 Claims, 1 Drawing Sheet

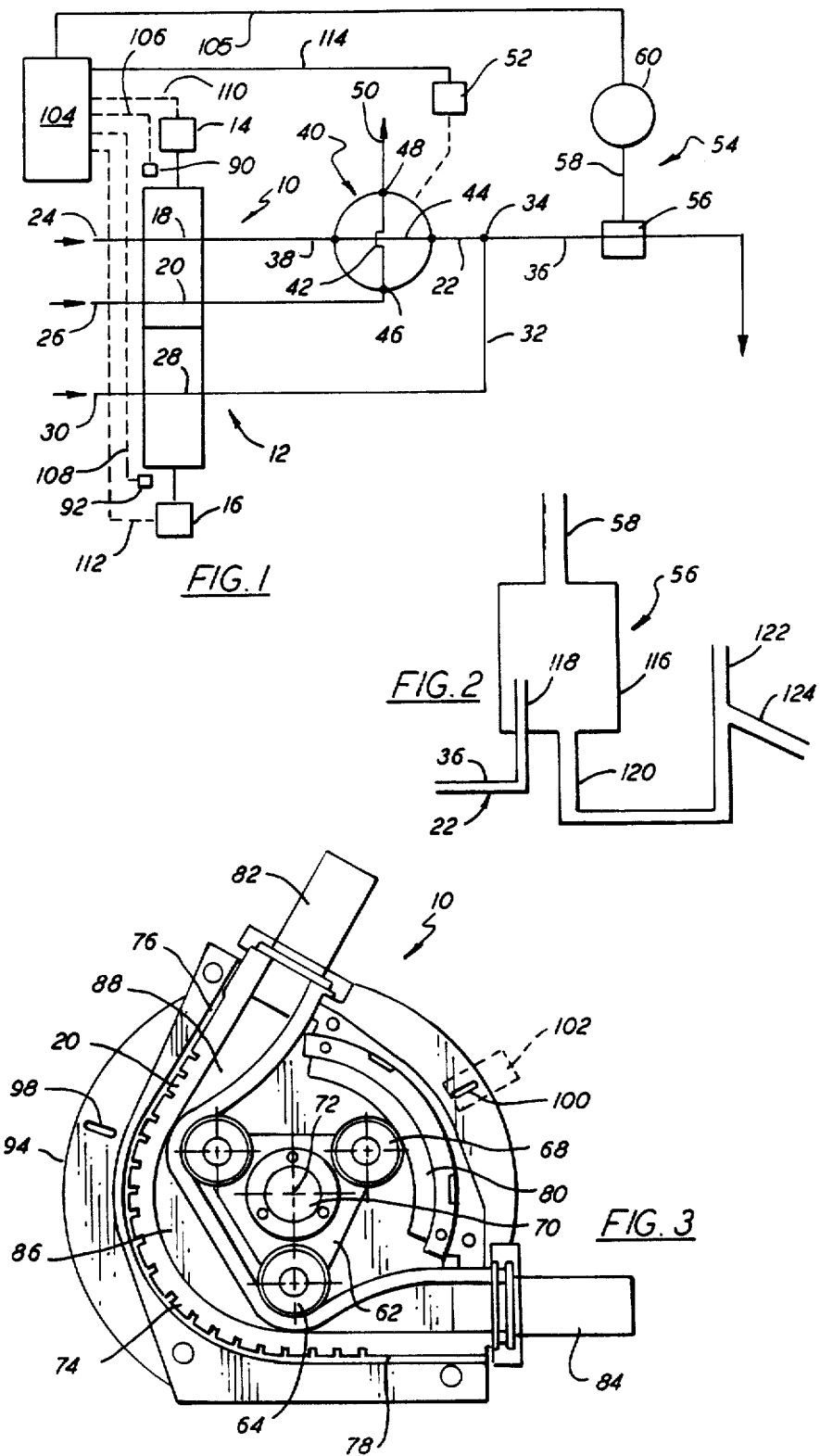

FLOW INJECTION APPARATUS FOR CARRYING OUT CHEMICAL ANALYSES

BACKGROUND AND SUMMARY OF THE INVENTION

This invention relates generally to chemical analysis and more particularly to a device and technique for flow injection analysis.

In a known device for flow injection analysis, a peristaltic pump is provided with parallel delivery in two hose conduits. In one of these hose conduits a reagent is delivered. A sample liquid is taken in through the other hose conduit which is connected to an intake tube which dips into a sample vessel. The sample vessels are arranged on an turntable. Thereby the different samples arranged in the sample vessels are taken in consecutively. The reagent hose conduit communicates with a relatively long conduit which leads through a photometer vessel to a waste vessel. A loop of tubing can be inserted between the intake tube and the peristaltic pump and can be optionally inserted by a changeover valve in the reagent flow between the reagent hose conduit and the reagent flow path to the photometer vessel, i.e., to measuring apparatus. Then a continuous flow of reagent flows through the conduit and to the photometer vessel. A definite volume of sample liquid is supplied, i.e., "injected", into this flow of reagent through the changeover valve. On the way to the photometer vessel in the relatively long conduit, the sample liquid has the opportunity to mix up and react with reagent. The change of color occurring thereby is measured. Such an arrangement for flow injection analysis offers an advantage in that it is quite easy to automate. In the described device the reagent serves at the same time as carrier liquid which rinses the sample liquid out of the tube circuit.

In another known device of the present type, the peristaltic pump delivers into three hose conduits at the same time. A first hose conduit is connected to a reagent reservoir and carries a flow of reagent as in the previously described device. A second hose conduit is connected to an intake tube which is arranged to take in sample liquid from sample vessels which are located on a turntable. A third hose conduit delivers air, such that the different samples are separated by air bubbles. The separation of the samples by air bubbles is effected upstream of the point at which reagent is injected into the sample liquid flow.

Hose pumps comprise a rotating carrier on which rollers are mounted in a regular arrangement about the rotational axis. A flexible hose is guided along a curved surface extending through an angular range about the rotational axis. The rollers contact the hose and compress it. Thereby, in one position of the carrier, a section or a chamber of the hose is closed towards the inlet-side and towards the outlet side. With further rotation of the carrier, the roller on the outlet side lifts off the curved surface to establish communication with the outlet. The liquid volume enclosed in the chamber is pressed out to the outlet by the roller on the inlet side. This roller on the inlet side of the section just mentioned simultaneously forms the roller on the outlet side of a following chamber. This chamber is enlarged when the last mentioned roller is moved along the hose by the carrier. Liquid is aspirated into the chamber until the following chamber is again closed towards the inlet by a further roller provided on the carrier. Then the described operation is repeated.

Usually such peristaltic pumps are driven by a conventional electric motor running at a constant rotary speed. The carrier rotates at a constant angular speed but the delivery of the peristaltic pump becomes nonuniform, i.e., when the rollers lift off the hose, the delivery decreases. The delivery of the peristaltic pump can also vary because of ageing of the hose, temperature variations and similar disturbances.

It is known to increase the rotational speed of the carrier when the rollers lift off to counteract this geometrically caused decrease of the delivery. A complex mechanical transmission is utilized to so increase the rotational speed which represents a very expensive solution.

Also, in devices of the present type, it is important to mix up liquids in exactly defined ratios and such nonuniformities of the delivery may cause measuring errors.

There are commercial sample inlet devices in which the sample liquid is passed through a changeover valve in a loop of tubing. Then this loop of tubing is connected to a carrier liquid flow path by means of a changeover valve. Then the loop of tubing is rinsed by the carrier liquid and the sample liquid is taken along by the carrier liquid. The changeover valve is reversed by a driving motor and for that purpose, the driving motor has to apply a relatively strong torque. The driving motor switches the changeover valve over from one switching position to another switching position between two stops. Known sample inlet devices of this type provide a sliding clutch between the driving motor and the changeover valve in order to ensure that the stops and the driving motor are not damaged. Such a sliding clutch is expensive and susceptible to trouble.

It is an object of the present invention to provide a new and improved flow injection device.

Another object of the invention to provide such a device wherein the peristaltic pump provides a delivery which is constant as a function of time.

Yet another object of the invention is to provide such a device which allows more flexible control of the liquid flows.

Other objects will be in part obvious and in part pointed out more in detail hereinafter.

Accordingly, it has been found that the foregoing and related advantages are attained in flow injection analysis apparatus having a measuring apparatus for measuring a looked-for element in an atomic state, a reagent conduit for conducting a flow of reagent to the measuring apparatus, and a sample injection apparatus for injecting a predetermined volume of sample liquid into the flow of reagent in the reagent conduit at a point upstream of the measuring apparatus. A peristaltic pump generates the flow of reagent and has a pump motor configured to be advanced stepwise in pumping the reagent. An electronic control controls the stepwise advancement of the pump motor to produce constant delivery through the reagent conduit. Preferably, the pump motor is a stepper motor and is controlled in a nonuniform step sequence to compensate the geometrically caused nonuniformity of delivery of the peristaltic pump, i.e, the nonuniformities of the delivery of the peristaltic pump caused by geometry are compensated by inverse nonuniformities of the angular rates. In an alternate configuration, a stepper motor is utilized to drive the changeover valve for alternately interconnecting a loop of tubing from the sample flow path to the carrier liquid path for injection into the reagent conduit.

Suitably the peristaltic pump motor is a stepper motor. Alternately, a normal electric motor could be used in which certain positions are predetermined, e.g., by means of an aperture disc and a photoelectric barrier, with a change over from one of these positions to the next being effected by suitable circuitry.

The motor which is arranged to be advanced stepwise allows an easy adaptation to the required modes of operation by program-controlled electronic control and to the uniformity of the delivery as well as with respect to the delivery flow and the taking into account of corrections.

One possibility of using a motor which is arranged to be advanced stepwise is that the step sequence of the motor is controlled non-uniformly by electronic control such that a constant delivery of the peristaltic pump is attained.

It is also advantageous when predetermined positions of the peristaltic pump can be detected by position detectors which provide position signals. These position signals may be supplied to the control electronics for synchronizing the non-uniformity of the step sequence with the delivery non-uniformity of the peristaltic pump caused by geometric conditions.

Another advantageous configuration is that the speed of the motor which is arranged to be advanced stepwise is controllable by an output signal of the measuring apparatus.

Another aspect of the invention is that the sample inlet device comprises a loop of tubing which is arranged to be connected optionally to the sample liquid flow path or to the conduit for the carrier liquid and that the changeover valve is arranged to be driven by a motor arranged to be advanced stepwise and is directly coupled thereto. In this way the necessity of a sliding clutch is avoided which according to prior art as described above involves high expenditure and is susceptible to trouble. Also, by such a motor, the changeover valve may be positioned gently in a definite valve position and stops are not necessary. Controlling is also effected by a program. Stops can be omitted. Furthermore, there is the possibility that the changeover valve is movable into more than two valve positions by the motor which is arranged to be advanced stepwise.

BRIEF DESCRIPTION OF THE DRAWINGS

FIG. 1 is a schematic circuit plan of a device for chemical analyses with peristaltic pumps, a loop of tubing with a changeover valve and a measuring vessel.

FIG. 2 is a schematic illustration of a gas separator in the device of FIG. 1.

FIG. 3 is a schematic illustration of a peristaltic pump in the device of FIG. 1.

DESCRIPTION OF THE PREFERRED EMBODIMENT

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the numerals 10 and 12 designate two peristaltic pumps. The peristaltic pump 10 is driven by a stepper motor 14 and the peristaltic pump 12 is driven by a stepper motor 16 as the peristaltic pump motors. The peristaltic pump 10 has two parallel hose conduits 18 and 20. The hose conduit 18 communicates with a conduit 22 which leads to a measuring apparatus 54. The hose conduit 18 is arranged for delivery of a carrier liquid different from the reagent, such as for example diluted hydrochloric acid, and has an inlet 24 connected to a carrier liquid reservoir. The hose conduit 20 is arranged for delivery of sample liquid and has an inlet 26 connected to a sample vessel.

The second peristaltic pump 12 comprises a hose conduit 28 having an inlet 30 connected to a reagent reservoir. The hose conduit 28 is connected to the conduit 22 by a reagent conduit 32 which opens into the conduit 22 at a point 34. Therefore, the carrier liquid plus reagent flow in the portion 36 of conduit 22 downstream of point 34.

A changeover valve 40 with a loop of tubing 42 is connected in the portion 38 of conduit 22 upstream of point 34. In the position of the changeover valve 40 illustrated in FIG. 1, a continuous connection is provided in the path of the conduit 22 from the hose conduit 18 through a valve passage 44 to the point 34 so that a carrier liquid flows to the measuring apparatus 54. Two ports 46 and 48 of the changeover valve 40 are connected to the hose conduit 20 and to a sample outlet 50, respectively. The connections 46 and 48 are connected to the two ends of the loop 42. Consequently, a sample liquid flow flows from the sample vessel through the hose conduit 20, port 46, loop 42, port 48 and sample outlet 50 to a waste vessel. In this way the loop 42 is filled with sample liquid.

The changeover valve 40 is driven by a directly coupled stepper motor so that a sliding clutch is not utilized.

When the changeover valve 40 is changed over to its second position so as to be rotated about 90 degrees relative to the position of FIG. 1, the loop 42 is positioned in the flow of the carrier liquid. The valve passage 44 connects the hose conduit 20 and the sample outlet. Thus the carrier liquid takes the sample liquid along from the loop 42 to carry it through conduit 22 to the measuring apparatus 54. In this way, a mixing-up of the sample liquid is caused at first with the carrier liquid and then with the reagent in the portion 36 of the conduit 22. Thereby a chemical reaction is initiated between a looked-for element of the sample liquid and the reagent. A measurement value of the concentration of the looked-for element in the sample liquid is obtained from this reaction in a measuring apparatus 54.

In the described preferred embodiment, the carrier liquid is diluted hydrochloric acid. The looked-for element in the sample liquid is a hydride forming element such as arsenic. A solution of sodium-boron-hydride (NaBH4) serves as reagent.

The measuring apparatus 54 comprises a gas separator 56. The gas produced in the gas separator is passed to a heated measuring cell 60 through a conduit 58.

In the portion 36 of the conduit 22, the sample liquid reacts with the sodium-boron-hydride and generates a hydride of the looked-for element of the sample liquid. Such a hydride is easily volatile. It is separated in the gas separator 56 as gas and flows through the conduit 58 to the measuring cell 60. In the measuring cell, decomposition of the hydride occurs such that the looked-for element is present in its atomic state in the measuring cell and is measured by a measuring light beam passed through the measuring cell according to the techniques of atomic absorption spectroscopy.

FIG. 3 shows a peristaltic pump 10. The peristaltic pump 10 comprises a carrier 62 having three rollers 64, 66 and 68 angularly spaced by 120 degrees. The carrier 62 rotates with a shaft 70 about an axis 72. A housing-fixed cylindric arcuate surface 74 extends in an arc of about 90 degrees about the axis of rotation 72. The arcuate surface 74 communicates at both ends with tangential plane surfaces 76 and 78. A cylindrical, arcuate supporting surface 80 arranged about the axis of rotation 72 is also provided on the opposite side of the surface 74.

The hose conduit 20 is guided along the surfaces 76, 74 and 78 from the inlet 82 to the outlet 84. The hose conduit 20 is compressed by the rollers 64, 66 and 68 as can be seen in FIG. 3. In the position illustrated in FIG. 3, the roller 66 compresses the hose conduit 20 on the inlet side such that a section of the hose conduit 20 is closed towards the inlet side. At the same time the roller 64 compresses the hose conduit 20 on the outlet side such that the section of the hose conduit 20 formed between the rollers 64 and 66 is also sealingly closed towards the outlet side. In this position a chamber 86 is formed which is sealingly closed towards both sides and which is filled with sample liquid. The chamber 86 opens towards the outlet 84 upon further counter-clockwise rotation of the carrier in FIG. 3. The roller 64 lifts off from the hose conduit 20. In contrast thereto the roller 66 further on firmly engaging the hose conduit 20 presses the hose further on firmly against the surface 74 and urges the sample liquid out of the chamber 86 into the outlet 84.

The roller 66 which forms the roller of the inlet side for the chamber 86 simultaneously forms a roller for the outlet side for a chamber 88 which has to be formed subsequently upstream of roller 66. Sample liquid is aspirated into this chamber.

Predetermined positions of the peristaltic pumps 10 and 12 can be detected by position sensors 90 or 92, respectively. The position sensors 90 and 92 provide position signals. FIG. 3 illustrates schematically that a disc 94 rotates with the peristaltic pump 10. The disc 94 has three radial slots 96, 98 and 100 angularly spaced by 120 degrees, only the slots 98 and 100 being shown in FIG. 3. These slots 96, 98 and 100 are scanned by a photoelectric barrier 102.

The position signals of the two position sensors are supplied to electronic control 104 as indicated by the broken lines 106 and 108, respectively. The electronic control 104 controls the stepper motors 14 and 16. This is indicated by the broken lines 110 and 112, respectively. Furthermore the electronic control 104 controls the stepper motor 52 which drives the changeover valve 40 as indicated by the line 114.

FIG. 2 shows the construction of the gas separator 56. The gas separator 56 comprises a vessel 116. The end 118 of conduit 22 extends into the vessel 116 and U-shaped tube with a leg 120 which branches off the bottom of the vessel 116. The other leg 122 of the U-shaped tube extends above the bottom of the vessel 116 and communicates with atmosphere. A conduit 124 branches off this leg 122 and leads to a waste vessel. The conduit 58 branches off the upper side of the vessel 116 and leads to the measuring vessel 60 (FIG. 1).

In operation, the delivery of a peristaltic pump driven at a constant rotary speed is non-uniform. The delivery decreases when the rollers 64, 66, and 68 lift-off from the hose conduit 20 (FIG. 3). This is counteracted by the electronic control 104, in that the frequency of the stepping pulses supplied to the stepper motor is varied during each revolution. Each time when the rollers lift-off from the hose conduit, the frequency of the stepping pulses and thus the rotary speed is increased such that a constant delivery results during the complete revolution of the peristaltic pump. This constancy is achieved by "software" without expensive mechanical means.

The rotary speed of the stepper motors 14 and 16 may be controlled in a simple manner by the frequency of the switching pulses.

The delivery of the peristaltic pump may vary by aging of the hose conduit or by temperature influences. The delivery of the peristaltic pump may be measured by suitable sensors and the sensor signals are supplied to the electronic control and the rotary speed of the peristaltic pump is controlled such that a desired delivery results independently of aging and external influences.

It is also possible to store in memory the empirically determined variation of the delivery by ageing of the hose conduit and to take this into account in the program control. In this manner, the influence of ageing, etc., may be at least approximately compensated.

It is also possible to control the stepper motors 14 and 16 through the electronic control by measurable variables of the measuring apparatus 54, e.g., in this case by the output signal of a spectrophotometer. Thus the flow of the reagent, for example, may be varied depending on this output signal supplied to electronic control 104 by line 105. Thereby "indirect" measurements are possible. The measuring value may be maintained constant for example, and the consumption of reagent necessary therefore may be determined. This corresponds to a titration.

It is also possible to control the flow to optimum values at which the measuring apparatus operates in its optimum measuring range. When the flows of carrier liquid and reagent are relatively strong the volume of sample liquid from the loop 42 and the gas generated by its reaction with the reagent is quickly delivered into the gas separator and there separates a strong gas flow of volatile hydrides during a short time. These hydrides are decomposed in the measuring cell and provide a "cloud of atoms" of the looked-for element. These atoms of the looked-for element have a high density in the cloud of atoms. Thereby the measuring light beam of the spectrometer is practically completely absorbed. The concentration of the looked-for element in the sample liquid can not be determined from this absorption, or only very imprecisely. When the flows of sample liquid and reagent are too small, the sample liquid from the loop 42 and the gas generated by the reaction of the sample liquid with the reagent are delivered only slowly into the gas separator. A small absorption of the measuring light beam in the measuring cell is obtained such that only a small absorption signal occurs. In between these conditions is an optimum value of the flow in which the absorption of the measuring light beam in the measuring cell depends with high sensitivity on the concentration of the looked-for element in the sample liquid.

Once a current supply for stepper motors is utilized in the electronic control, the changeover valve may be driven by such a stepper motor. Thereby the sliding clutch may be omitted. Also the stops may be omitted. The changeover valve can be switched in more than two valve positions. That permits several samples to be delivered through different sample conduits into the loop 42.

As can be seen, a new and improved flow injection apparatus and technique is provided which allows flexible control of liquid flow and peristaltic pump delivery which is constant as a function of time.

As will be apparent to persons skilled in the art, various modifications and adaptations of the structure above described will become readily apparent without departure from the spirit and scope of the invention, the scope of which is defined in the appended claims.

What is claimed is:

1. A flow injection chemical analysis apparatus comprising
   means for measuring an element in an atomic state,
   reagent conduit means for conducting a flow of reagent to said measuring means,
   sample inlet means for injecting a predetermined volume of sample liquid into the flow of reagent in said reagent conduit means at a point upstream of said measuring means,
   peristaltic pump means for generating a flow of reagent through said reagent conduit means, said pump means having a peristaltic pump motor configured to be advanced stepwise in pumping reagent, and
   means for controlling the stepwise advancement of said peristaltic pump motor to produce constant delivery over a single revolution through said reagent conduit means.

2. The device of claim 1 wherein
   said pump motor of said peristaltic pump means for generating a flow of reagent is a first stepper motor and further comprising
   a second peristaltic pump means for generating a flow of carrier liquid and a flow of sample liquid which has a second stepper motor to be advanced stepwise,
   a connection conduit between said sample inlet means and said reagent conduit means,
   said second pump means having first and second conduits, said first conduit being adapted to carry carrier liquid to said connection conduit and said second conduit being adapted to carry sample liquid to said connection conduit, and
   said reagent conduit means being connected to said connection conduit downstream from said smaple inlet means.

3. The device of claim 1 wherein said peristaltic pump motor is a stepper motor.

4. The device of claim 3 wherein said control means controls said stepper motor in a nonuniform step sequence.

5. The device of claim 1 wherein said sample inlet means comprises
   carrier liquid conduit means for conducting carrier liquid and sample liquid to said measuring means,
   sample conduit means for conducting sample liquid along a predetermined flow path,
   a loop of tubing alternately interconnectable in first and second positions by a change-over valve, said loop being interconnected in the predetermined flow path of sample liquid in said first position and being interconnected to the carrier liquid conduit means in said second position, and
   motor means for driving said change-over valve between said first and second positions, said motor means being configured for stepwise advancement and being directly coupled to said change-over valve.

6. The device of claim 5 wherein said change-over valve is configured to be driven into more than two operating positions by said motor which is arranged to advance stepwise.

7. The device of claim 1 further comprising speed control means for controllably varying speed of said peristaltic motor.

8. The device of claim 7 wherein said speed control means is responsive to output signals from said measuring means.

9. A flow injection chemical analysis apparatus comprising:
   means for measuring an element in an atomic state,
   reagent conduit means for conducting a flow of reagent to said measuring means,
   sample inlet means for injecting a predetermined volume of sample liquid into the flow of reagent in said reagent conduit means at a point of said measuring means,
   peristaltic pump means for generating a flow of reagent through said reagent conduit means, said pump means having a peristaltic pump stepper motor configured to be advanced stepwise in pumping reagent,
   position sensor means for detecting predetermined rotational positions of said peristaltic pump means to generate position signals, and
   means for controlling the stepwise advancement of said peristaltic pump stepper motor to produce constant delivery over a single revolution through said reagent conduit means.

10. The device of claim 9 wherein said sensor means is connected to said control means, said control means having means for controlling said stepper motor in a nonuniform step sequence and means for synchronizing the nonuniformity of the motor step sequence to geometrically-caused nonuniformity of delivery of the peristaltic pump means over a single revolution of said stepper motor.

11. The device of claim 10 further comprising speed control means for controllably varying the speed of the peristaltic pump stepper motor responsive to output signals from said measuring means.

12. The device of claim 10 wherein said sample inlet means comprises
   carrier liquid conduit means for conducting carrier liquid and sample liquid to said measuring means,
   sample conduit means for conducting sample liquid along a predetermined flow path,
   a loop of tubing alternately interconnectable in first and second positions by a change-over valve, said loop being interconnected in the predetermined flow path of sample liquid in said first position and being interconnected to the carrier liquid conduit means in said second position, and
   motor means for driving said change-over valve between said first and second positions, said motor means being configured for stepwise advancement and being directly coupled to said change-over valve.

13. The device of claim 12 wherein said change-over valve is configured to be driven into more than two operating positions by said motor which is arranged to advance stepwise.

* * * * *